United States Patent [19]
Trees

[11] 3,982,716
[45] Sept. 28, 1976

[54] MEDICAL BOTTLE HOLDER

[76] Inventor: Alonzo Trees, 300 Carrington Road, Waterloo, Iowa 50701

[22] Filed: Sept. 24, 1975

[21] Appl. No.: 616,124

[52] U.S. Cl. .......................... 248/206 A; 248/311.3
[51] Int. Cl.² ................ A61B 19/00; A47G 29/02; B65D 23/10
[58] Field of Search ........ 248/311 A, 311 R, 206 A; 222/181, 185; 211/88, 75

[56] References Cited
UNITED STATES PATENTS

| | | | |
|---|---|---|---|
| 2,170,182 | 8/1939 | Anthony | 222/181 |
| 2,677,372 | 5/1954 | Barnish | 248/311 A UX |
| 2,689,066 | 9/1954 | Budnik | 222/181 X |
| 2,718,985 | 9/1955 | Tamminga | 222/185 X |
| 3,201,072 | 8/1965 | DuBois | 248/206 A X |
| 3,254,804 | 6/1966 | Grant | 222/185 |
| 3,578,199 | 5/1971 | Duncan | 248/311 R X |
| 3,840,261 | 10/1974 | Fulkerson | 248/311 R |

FOREIGN PATENTS OR APPLICATIONS

| | | | |
|---|---|---|---|
| 470,641 | 1/1951 | Canada | 248/311 A |
| 295,919 | 8/1928 | United Kingdom | 222/181 |

*Primary Examiner*—J. Franklin Foss
*Attorney, Agent, or Firm*—Shoemaker and Mattare, Ltd.

[57] ABSTRACT

A holder for temporarily supporting a bottle containing hypodermically injected medication. The holder is magnetically attached to a supporting surface, and securely supports the bottle so that both hands of the user are free to manipulate a syringe to withdraw the proper dosage from the bottle.

2 Claims, 9 Drawing Figures

MEDICAL BOTTLE HOLDER

BACKGROUND OF THE INVENTION

The present invention relates to holding devices for supporting a bottle on a wall, and, more particularly, to devices for supporting medical bottles which contain hypodermically injected medication.

It is often awkward and difficult for the average person to fill a hypodermic syringe safely because one hand is almost completely occupied with holding the medical bottle in an inverted position to prevent air from entering the syringe. Therefore, the operations of inserting the hypodermic needle upwardly into the small access area of the container and withdrawing the fluid into the syringe must both be performed by the other hand. Thus, to assure that only the prescribed dosage is withdrawn without entrapped air, a high degree of dexterity and hand-eye coordination is required. This can be particularly troublesome for older people whose hands are not steady and well coordinated or who may have poor eyesight, arthritis, or other adverse effects of old age. Many medicines, particularly insulin, must be maintained at the proper temperature. It is often difficult to take such medication to work, or to travel with it. However, such medication must somehow be transported to protect the life of the user.

There are known insulin bottle holders which mechanically mount an insulin bottle onto a wall or other surface. However, these bottle holders generally comprise at least two distinct and separate parts, one of which is permanently and mechanically attached to a wall or other surface and which is attached to the bottle holding body by holding means, such as tapered lugs. These holding means must be released by mechanical cam levers. These known devices are therefore complex and hence expensive. Furthermore, such devices are not amenable to being transported to work or on vacation and require a degree of manual dexterity to operate which may not be possessed by certain people, particularly elderly people.

SUMMARY OF THE INVENTION

The medical bottle holder embodying the present invention is simple to operate and is stationarily held on a supporting surface without requiring a permanent attachment thereto.

One embodiment of the present invention comprises a cylindrical body section for supporting the bottle containing the medication. The holder body has a magnet which is attached to the body either adhesively or by elements integral with the body, and the medical bottle is inserted into the holder for attachment to a magnetically permeable wall or the like. Thus, the holder can be temporarily attached to a supporting surface and yet securely hold the bottle in the desired position. The temporary attachment using the magnet is easy and expeditious. The holder can be made of a non-brittle material, such as Plexiglass, or metal, or insulating material to protect the glass medical container from damage if it is dropped, and to provide easy transportation or storage of medication. The holder has a pivotable end cover on one end which is easily moved into and out of position to enable the medicine containing bottle to be received in the holder body and be securely held therein while a syringe is being forced into the bottles. Elderly persons, or other people with below average manual dexterity, can thus easily open and close the holder.

Another embodiment of the invention comprises a magnet attached directly to the medicine containing bottle to permit the bottle to be readily attached to any magnetically attachable metal object, such as a bathroom medicine cabinet door. The attachment is either adhesive or by holding means integral with the bottle. As in the first embodiment, the bottle is maintained in an inverted position for easy cooperation with a syringe. The user thus has both hands free to insert the syringe needle and withdraw the medication into the syringe. Thus, the exact dosage, without any entrapped air, can be easily withdrawn. In this embodiment, the medical container can be disposed of after use.

Yet another embodiment of the invention comprises a magnet attached to a brace or other container holding device which has straps which are then secured about the medicine container. When the container is empty, the container is discarded and the container holder is reused.

OBJECT OF THE INVENTION

Accordingly, it is a main object of the present invention to hold a bottle containing hypodermically injected fluid in an inverted position in order to leave the user's hands free to manipulate a syringe.

It is a further object of the present invention to provide a simple and inexpensive device which is easily used and can be temporarily attached to a variety of supporting surfaces.

It is yet another object of the present invention to protect an insulin bottle against damage during storage and/or transportation thereof.

It is a specific object of the present invention to provide a medical bottle holder which is magnetically attachable to a supporting surface.

BRIEF DESCRIPTION OF THE DRAWINGS

FIG. 4a shows an exploded perspective of another embodiment of the present invention;

FIG. 4b shows a detail of the holder shown in FIG. 4a;

DESCRIPTION OF THE EMBODIMENTS OF THE PRESENT INVENTION

Figure 1:
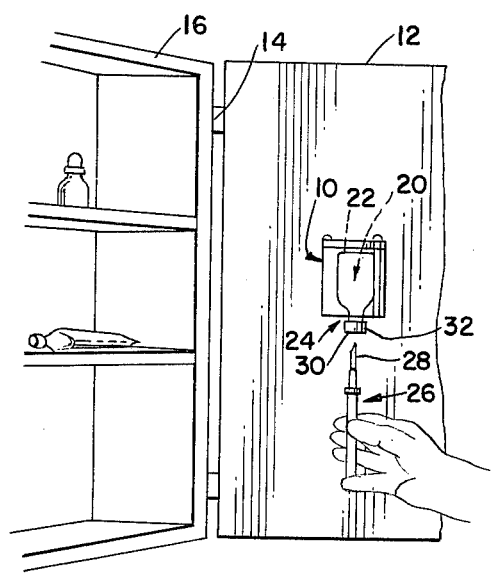
FIG. 1 shows the medical bottle holder mounted on a supporting structure in accordance with the teachings of the present invention.

Shown in FIG. 1 is a holder 10 mounted on the inner wall of a door 12, such as a medicine cabinet door which is hingeable connected by hinges 14 to a medicine cabinet 16. The holder 10 stationarily supports a medicine container 20, which, in the preferred embodiment is a bottle containing hypodermically injected medication, such as insulin. The container 20 has a base 22 and a forward end 24, and is held in the inverted position by holder 10. A syringe 26 having a piercing needle 28 can therefore be held in the position shown in FIG. 1, wherein the needle 28 can be inserted through puncturable seal 30 held on forward end of the bottle 24 by retaining ring 32 or the like. The holder 10 supports the bottle or container 20, thus freeing both hands of the user to manipulate the syringe 26 to withdraw the proper dosage of medication without entrapped air therein.

Figures 4A, 4B:
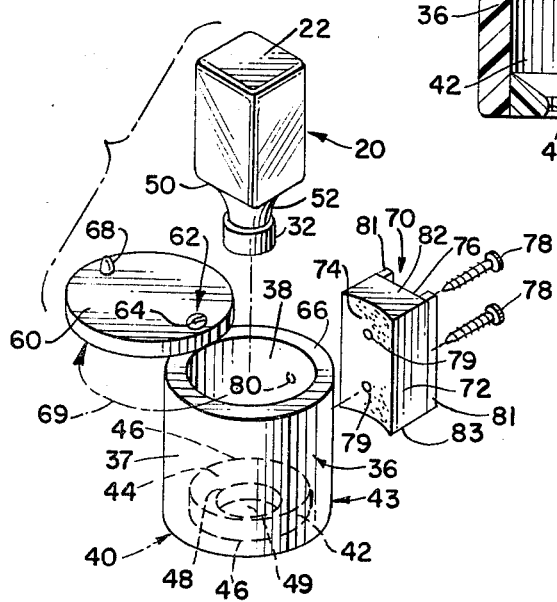
Figure 5:
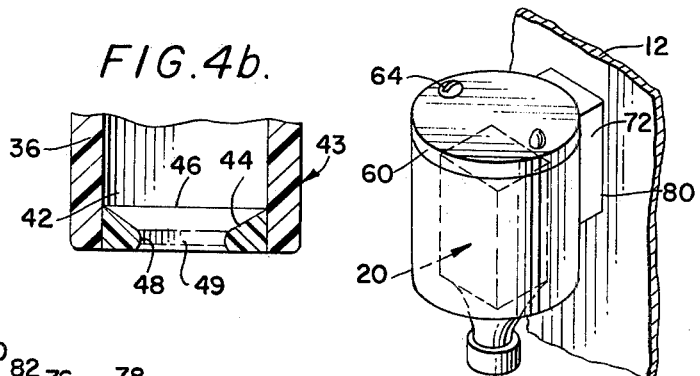
FIG. 5 shows the FIG. 4 embodiment mounted on a supporting surface in accordance with the teachings of the present invention.

Further details of the embodiment of the holder shown in FIG. 1 are illustrated in FIGS. 4 and 5. As shown in FIG. 4, the holder 10 comprises a hollow cylindrical body section 36 having a side wall 37 and an axial bore 38 which forms a chamber therein. An end cover or plug 40 is located at one end of body 36 and is mounted therein and will support the container 20 in the position shown in FIG. 1. The plug comprises a body 42 fixed in end 43 of body section 36 and has a frusto-conically shaped abutment shoulder 44 extending therein from horizontal ledge 46 to exit lip 48 located near the plane of the lower terminal end of the holder 10 and forms a neck receiving passage 49 through which neck 52 fits when the container 20 is positioned in the holder 10.

As shown in FIG. 4a, container 20 has a shoulder 50 and a neck 52 to which is attached the retaining ring 32. Therefore, when the container 20 is held in holder 10, shoulder 50 abuts shoulder 44 of the plug 40 and neck 52 extends outwardly of the holder 10 through exit opening 48, as shown in FIGS. 1 and 5.

As shown in FIG. 4a, a disc-shaped closure cap 60 is pivotally mounted at end 62 of the container housing 36. A pivot means, such as a screw 64, attaches the cover 60 to edge 66 of the housing 36. As shown, a knob 68 is positioned on the cover 60 to act as a finger grip so that the cover 60 can be easily rotated from the open position shown in FIG. 4a to the closed position shown in FIG. 5. Arrow 69 denotes the direction of the opening movement of cap 60. In the closed position, the cover 60 engages base 22 of the container 20 so that the container is supported in the position shown in FIGS. 1 and 5, whereby the container 20 is held securely so that needle 28 of syringe 26 can be inserted through puncturable seal 30.

The holder 10 can be made of a non-brittle material, such as Plexiglass, metal, or the like, and is reusable. Thus, when container 20 is empty, it is simply removed from the holder 10 and replaced by a new container 20.

As shown in FIGS. 4a and 5, the body section 36 is mounted on a wall or support surface, such as door 12, by a mounting means 70. The mounting means 70 comprises a support 72 having an engaging face 74 shaped to correspond to the outer surface of body 36 and a rear surface 76 shaped to correspond to the mounting surface, such as door 12. Securing means, such as screws 78 fitting through screwholes 79 and 80 are used to couple the mounting means 70 to the body 36. The magnet, or mounting means can also be integrally molded onto the body 36. Supported on face 76 of the mounting means are magnets, such as elongated bar magnets 81 for coupling the housing 10 to the supporting surface.

In the preferred embodiment, the length of mounting means 72 is approximately equal to that of the body section 36, with ends 82 and 83 coplanar with edge 66 and end 43, respectively. The holder 10 can be made of a plastic or other transparent material so that the amount of medicine remaining in container 20 is readily determinable. Furthermore, the body 36, or the entire holder 10, can be made of an insulating material so that insulin contained in bottle 20 can be transported from place to place without endangering the integrity of the insulin after the bottle has been removed from a refrigerated environment.

Figure 2:
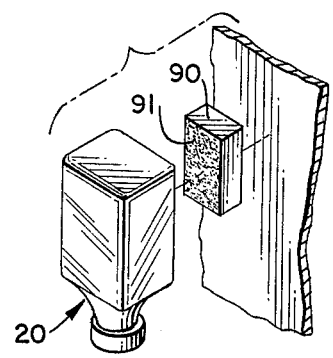
FIG. 2 shows an exploded perspective of one embodiment of the present invention.
Figure 3:
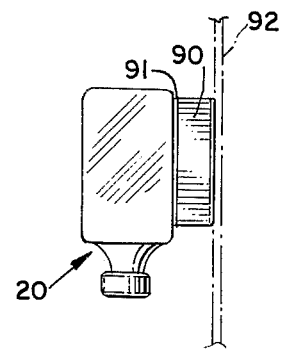
FIG. 3 shows the FIG. 2 embodiment mounted on a supporting surface in accordance with the teachings of the present invention.

Shown in FIGS. 2 and 3 is another embodiment of the present invention, wherein the container 20 is adhesively secured to a magnet 90 by adhesive means 91. As shown in FIG. 3, the magnet 90, having the container 20 fixed thereto, is attached to a supporting surface, such as wall 92. In the embodiment shown in FIGS. 2 and 3, the container 20 is permanently attached to the magnet 90, and the entire unit, comprising container 20 and magnet 90, is discarded after use. A mounting means similar to mounting means 70 can also be used.

Figure 8:
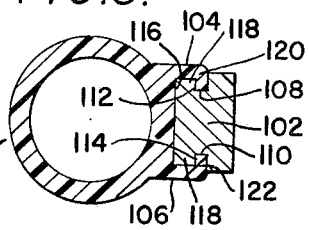
FIG. 8 shows a magnet securing means integrally mounted to a medicine container in accordance with the teachings of the present invention.

Shown in FIG. 8 is an embodiment of the present invention wherein a medicine container 100 has a magnet 102 slidably mounted thereon. The magnet can be either permanently or temporarily affixed to container 100. As shown in FIG. 8, the container 100 has a pair of flanges 104 and 106 formed integrally therewith. The flanges 104 and 106 are longitudinally disposed on the container 100 and have opposing lips formed by longitudinal edges 108 and 110, respectively, and shoulders 112 and 114, respectively, which form with surface 116 of the container 100 channels 118 into which lip engaging slots 120 and 122 on the longitudinal side edge of magnet 102 are engaged. The container 100 in the FIG. 8 configuration is discarded after use and a replacement container is engaged on magnet 102. Thus, while the magnet 102 may be reusable, the containers are not. Further, the removable magnet configuration of FIG. 8 can be used on a holder as in FIGS. 3 and 5, if desired, to support a bottle.

Figure 7:
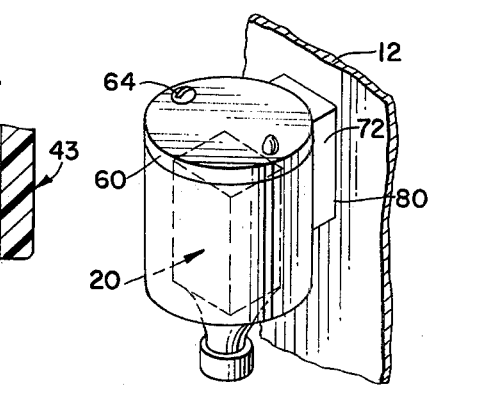
FIG. 7 shows an exploded perspective of the FIG. 6 embodiment of the present invention.
Figure 6:
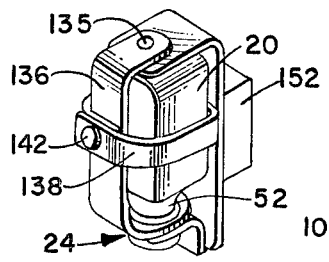
FIG. 6 shows another embodiment of the present invention.

FIGS. 6 and 7 show another embodiment of the present invention, wherein the medicine container 20 is supported in a plurality of straps on the holder for mounting on the supporting surface. As shown in FIG. 7, an L-shaped brace 129 has a bend 130, side leg 132 with a free end 133, and a top leg 134 with a free end 135, and has longitudinal strap 136 and transverse strap 138 mounted on legs 134 and 132, respectively. As shown in FIG. 7, the longitudinal strap 136 is flexible and has a deformable hole 140 in one end thereof and is attached to the free end of top leg 134 at the other end thereof by rivet 141. Transverse strap 138 has a protrusion 142 on one end thereof and snap lock 144 on the other end thereof, and is attached to side leg 132 at a midpoint intermediate the two ends thereof and intermediate bend 129 and free end 133. A bridle 146 comprising a deformable hole 148 in one end is mounted at the other end 149 on free end 133 of side leg 132. A magnet 152 is attached to the side leg 132 and is used to attach the brace 130 to a mounting surface. As in the other embodiments, a mounting means similar to mounting means 70 can be used.

As shown in FIG. 6, flexible strap 136 is stretched around the medicine container 20 in a longitudinal direction, and deformable hole 140 is secured around neck 52 of the medicine container. The forward end 24 of the medicine container is then forced through deformable hole 148. The transverse strap 138 is then secured about the container 20 by forcing protrusion 142 into lock 144 to latch same in the position shown in FIG. 6. The straps 136 and 138 may be resilient to facilitate the above-discussed attachment of container 20 to the brace 129. Resilient materials suitable for use for the straps 136 and 138 are plastic, elastomers, or the like.

In the FIGS. 6 and 7 configuration, the container 20 may be either reusable or throw-away. This embodiment, like the others, supports the container in a stable position thereby allowing the user to have both hands free to control the syringe 26. Furthermore, this configuration, like the others, is simple and can easily be used on various supporting surfaces without being permanently attached thereto, and is easily manipulated by one having less than average manual dexterity.

As this invention may be embodied in several forms without departing from the spirit or essential characteristics thereof, the present embodiment is, therefore, illustrative and not restrictive, since the scope of the invention is defined by the appended claims rather than by the description preceding them, and all changes that fall within the metes and bounds of the claims or that form their functional as well as conjointly cooperative equivalents are, therefore, intended to be embraced by those claims.

I claim:
1. A holder for supporting a medicine container having hypodermically injected medication therein and including a sealed mouth section, a shoulder section and a neck connecting the mouth and shoulder sections, the holder comprising:
a hollow cylindrical body made of non-brittle, insulating material and having first and second ends joined by a side wall and a chamber defined therein for accommodating the medicine container;
an end cover including a plug mounted on said body first end having a neck receiving passage for permitting the medicine container mouth section and neck to project through said end cover with the mouth section exterior of the housing when the container is accommodated in said chamber, said cover defining a shoulder interiorly of the housing for abutting the medicine container shoulder to support the medicine container in a stationary manner in said chamber with the mouth section projecting through said end cover, said plug including a plug end positioned inside said chamber with said shoulder being a frusto-conically shaped surface connecting said plug end and said neck receiving passage;
a circular closure cap pivotally connected at a side edge thereof to said body second end for pivotal movement in a plane parallel to a plane containing said second end so that said cap slidably engages said second end to selectively cover and uncover said body second end to enable a medicine container to be placed in and removed from said chamber and to hold the container in place in said chamber when a piercing needle is being forced through the sealed mouth section;
a pivot pin comprised of a screw-like element penetrating through said cap and into said container side wall to form a pivot axis for said cap which is essentially parallel to the longitudinal axis of said cylindrical body for pivotally connecting said cap to said body;
means for pivoting said closure cap;
an elongated magnet on one side of said body detachably securing said body to a supporting means; and
means fixing said magnet to said body so that said magnet is longitudinally aligned with said body, attaching means being fixed to said magnet for essentially the entire length thereof and engaged against said body for essentially the entire length thereof so that said body and said magnet are fixed together for essentially the entire lengths thereof and are essentially immovable with respect to each other thereby adapting said holder to be fixed to said supporting means over essentially the entire length of said holder so that the medicine container will be rigidly and fixedly held in place when it is accommodated in said chamber with said closure cap closed.

2. The holder of claim 1, including a plurality of elongated magnets fixed to said magnet mounting means.

* * * * *